United States Patent [19]

Holt

[11] Patent Number: 5,866,791
[45] Date of Patent: Feb. 2, 1999

[54] MODIFICATION OF LIGNIN SYNTHESIS IN PLANTS

[75] Inventor: Karen Anne Holt, Shurlock Row, United Kingdom

[73] Assignee: Zeneca Limited, London, England

[21] Appl. No.: 613,942

[22] Filed: Mar. 13, 1996

[30] Foreign Application Priority Data

Oct. 25, 1998 [GB] United Kingdom .................. 9521848

[51] Int. Cl.$^6$ ............................. A01H 4/00; C07H 21/04; C12N 5/14; C07K 14/415
[52] U.S. Cl. .......................... 800/205; 800/200; 800/250; 435/6; 435/69.1; 435/91.4; 435/320.1; 435/410; 435/419; 530/377; 536/23.6; 536/24.5
[58] Field of Search ..................................... 800/200, 205, 800/250; 435/69.1, 320.1, 419, 410, 6, 91.4; 536/23.6, 245.5; 530/377

[56] References Cited

U.S. PATENT DOCUMENTS 5,451,514  9/1995  Boudet et al. .

FOREIGN PATENT DOCUMENTS 0 271 988  6/1988  European Pat. Off. .
93/05160  3/1993  WIPO .

OTHER PUBLICATIONS

Smith, C. J. S., et al., Nature, "Antisense RNA inhibition of polygalacturonase gene expression in transgenic tomatoes", vol. 334, 1988, pp. 724–726.

Bevan, M., Nucleic Acids Research, "Binary Agrobacterium vectors for plant transformation", vol. 12, No. 22, 1984, pp. 8711–8721.

De Block, M., Plant Physiol., "Factors Influencing the Tissue Culture and the *Agrobacterium tumefaciens*–Mediated Transformation of Hybrid Aspen and Clones", vol. 93, 1990, pp. 1110–1116.

Frame, B. R., et al., The Plant Journal, "Production of fertile transgenic maize plants by silicon carbide whisker–mediated transformation", vol. 6, No. 6, 1994, pp. 941–948.

Lewis, N. G., et al., Annu. Rev. Plant Physiol. Plant Mol. Biol., "Lignin: Occurrence, Biogenesis and Biodegradation", vol. 41, 1190, pp. 455–496.

Smith, C.J.S., et al., Plant Molecular Biology, "Inheritance and effect on ripening of antisense polygalacturonase genes in transgenic tomatoes", vol. 14, 1990, pp. 369–379.

Bevan, M., The Embo Journal, "Tissue and cell–specific activity of a phenyl–alanine ammonia–lyase promoter in transgenic plants", Vo 8, No. 7, 1989, pp. 1899–1906.

*Primary Examiner*—Jeffrey Stucker
*Assistant Examiner*—Phuong T. Bui
*Attorney, Agent, or Firm*—Liza D. Hohenschutz

[57] ABSTRACT

The synthesis of lignin by plants, particularly cereal and forage crops, is modified by genetic transformation with a construct which includes a DNA sequence which modifies the activity of the enzyme cinnamyl coenzyme A reductase (CCR). Sequence-ID-1 is the CCR sequence from *Zea mays*.

10 Claims, 2 Drawing Sheets

MODIFICATION OF LIGNIN SYNTHESIS IN PLANTS

This invention relates to the improvement of plants by the modification of lignin biosynthesis, particularly, but not exclusively, the improvement of digestibility of fodder crops. More specifically, the invention relates to the gene encoding cinnamyl coenzyme A reductase from *Zea mays*.

Grassland farmers, and farmers of other fodder crops, face a difficult decision each year about when to cut their crops for conservation. All grass varieties of agricultural importance suffer from the disadvantage that during the normal increase in dry matter yield with growth, the digestibility decreases. The farmer, therefore, has, to compromise between a lower yield of highly digestible material and a higher yield of less digestible material. Another limitation is that harvesting at optimum maturity may be prevented by unfavourable weather. If the decline in digestibility could be controlled or delayed, higher yields of highly digestible material could be obtained and the prevailing weather conditions would not play such a major role in determining the quality of the harvested crop.

Digestibility of fodder crops is determined, among other factors, by the amount and quality of lignin deposition which has taken place during growth of the plants and the degree of secondary modification of lignin deposited. Beside cellulose and other poly-saccharides, lignins are an essential component of cell wall in tissues like the sclerenchyma and the xylem of vascular plants. They play an important role in the conducting function of the xylem by reducing the permeability of the cell wall to water. They are also responsible for the rigidity of the cell wall, and, in woody tissues, they act as a bonding agent between cells, imparting to the plant a resistance towards impact, compression and bending. Finally, they are involved in mechanisms of resistance to pathogens by impeding the penetration or the propagation of the pathogenic agent.

Lignins are not only important in the productivity and performance of field crops but are also of great importance in trees for paper making. Considerable energy and chemical input is required to loosen, dissolve and remove lignin from the cellulose fibre which is required for paper making. In addition to these instances in which lignins present a constraint on the use of crop plants, lignins are also used as feedstocks for the preparation of speciality chemicals such as phenolics which can be used as precursors in chemical synthesis. Thus lignins and their biological and chemical modification are important.

It is one of the objects of the present invention to provide a biotechnological procedure for the modification both lignin content and lignin composition in plants.

Lignins are the product of a dehydrogenative polymerisation of three primary precursors: the trans-coniferyl, trans-sinapyl and trans-p-coumaryl alcohols. The monomers can occur in lignins in different proportions and with different types of links both with each other and with the surrounding cell wall polysaccharides, thus producing a wide variety of polymers. These polymers, or "lignin cores" are always associated covalently with hemicelluloses. Most lignins also contain varying amounts of aromatic carboxylic acids in ester-like combinations. Such differences in the structure of lignins are usually found in plant species. However, differences in the composition of lignins, and even in the binding to the primary and secondary cell walls, can also occur in the same plant, between different tissues of different ages. The biosynthesis of lignin monomers (monolignols) is a part of the phenylpropanoid biosynthesis pathway, which is also responsible for the production of a wide range of compounds including flavonoid pigments, isoflavonoids, coumarin phytoalexins and cell division promoting dehydrodiconiferyl glucosides.

Phenylalanine is deaminated to produce cinnamic acid. This acid is then transformed by hydroxylation and methylation reactions, thus producing different acids substituted on the aromatic ring. The enzyme catalysing the methylation steps is O-methyl transferase (OMT). O-methyltransferases (S-adenosyl-L-methionine: O-methyltransferases; EC 2.1.1.6) thus play an important role in the biosynthesis of monolignols. By the O-methylation of caffeic acid and 5-hydroxyferulic acid, OMTs introduce one and two methoxy groups in the lignin monomers, respectively. The resulting two phenolics, ferulic acid and sinapic acid, respectively, are the precursors of coniferyl alcohol and sinapyl alcohol which are together with coumaryl alcohol substrates for peroxidases (Lewis and Yamamoto, 1990).

The previous methylation reactions are also used in the synthesis of several other phenolic compounds. However, in those cells which are dedicated to the production of lignins such as vascular xylem cells of plants, the OMT plays a crucial role in the production of the phenolic precursors incorporated into the lignin polymer. The cinnamyl alcohols, synthesised in the cytoplasm, are then transported to the cell wall where they are polymerised by peroxidase in the presence of hydrogen peroxide.

When the surface growth of the cell ceases, it is followed by a phase of wall thickening (secondary wall formation). Lignification takes place during this phase. It starts in the cell comers and extends along the middle lamella, through the primary wall and, finally, to the secondary wall. External factors can induce qualitative and quantitative modifications in lignification. The synthesis of new types of lignins, sometimes in tissues which are not normally lignified, may be induced by infection with pathogenic microorganisms. Lignification is stimulated by light, as well as by low calcium levels, by boron, by mechanical stress and by infection.

Our International Patent Application Number WO 93/05160 describes the cloning of O-methyltransferases (OMTs). Previously three different OMTs (OMT I, OMT II, and OMT III) have been purified from tobacco. OMT I used mainly caffeic acid and 5-hydroxyferulic acid as a substrate and is the OMT actively present in healthy plants. OMT II and OMT III have a broader substrate specificity and also use catechol as substrate. Upon infection with TMV, an increase in activity of all three OMTs was shown. Based on this observation, it has been postulated that the OMT I is specifically involved in lignification, whereas OMT II and OMT III have a function in generating a lignin barrier upon infection. The importance of methylation in monolignol biosynthesis is well illustrated in brown-rib corn mutants. These plants exhibit a reduced lignin content and accumulate 5-hydroxyferulic acid) due to a low O-methyltransferase activity. Thus OMTs could be potential targets for modulation of lignification through the use of recombinant DNA technology.

Thus, plants with a reduced amount of lignin would be more efficiently used as a forage for cattle. The yield of milk and meat would be therefore increased. Furthermore, lignin may have a negative effect on plant growth. Thus, a reduction of the lignification in crops such as wheat, oilseed rape, sugar beet or maize might presumably increase the grain yield. Trees with reduced lignin contents or altered lignin structure will lead to a reduction in the cost of the paper as less lignin will have to be removed during the pulping process. On the other hand, novel papers may be produced due to the purity of cellulose fibre which could otherwise not be produced.

Reduction of lignification can be achieved by the application of chemical inhibitors to plants. However, a more effective method controlling lignin deposition and structure is the inhibition of expression of the CAD gene using antisense RNA. The cloning of CAD and its use in this way is described in out International Patent Application Number WO 93/05159. Antisense RNA technology is an appropriate molecular biology approach to the inhibition of lignification. An antisense RNA is an RNA produced by the transcription of the non-coding DNA strand (nonsense). Thus, antisense RNA has the same sequence as the coding DNA strand and is complementary to the mRNA product of a specific gene.

As is well known, a cell manufactures protein by transcribing the DNA of the gene for that protein to produce RNA, which is then processed (e.g. by the removal of introns) into messenger RNA and finally translated by ribosomes into protein. This process may be inhibited by the presence in the cell of "antisense RNA". Therefore, as used herein, the term "antisense RNA" means an RNA sequence which is complementary to a sequence of bases in a MRNA: complementary in the sense that each base (or a majority of bases) in the antisense sequence (read in the 3' to 5' sense) is capable of pairing with the corresponding base (G with C, A with U) in the MRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or lead to degradation of the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to down-regulate the expression of specific plant genes has been described, for example in European Patent Publication No 271988. Reduction of gene expression has led to a change in the phenotype of the plant: either at the level of gross visible phenotypic difference e.g. lack of lycopene synthesis in the fruit of tomato leading to the production of yellow rather than red fruit or at a more subtle biochemical level e.g. change in the amount of polygalacturonase and reduction in depolymerisation of pectins during tomato fruit ripening (Smith et al, Nature, 334, 724–726, 1988; Smith et al, Plant Mol Biol 14, 369–380, 1990). Thus antisense RNA has been proven to be useful in achieving down-regulation of gene expression in plants.

An object of the present invention is to provide plants having an altered ability to synthesise lignin.

According to the present invention there is provided a cDNA encoding cinnamyl coenzyme A reductase from *Zea mays*, contained in the clone pMCCR6A and variants thereof such as are permitted by the degeneracy of the genetic code or the functional equivalents thereof.

The invention further provides a recombinant DNA comprising the DNA aforesaid under control of a transcriptional control sequence operative in plants.

The said recombinant DNA may be used for the down-regulation of lignin biosynthesis in which case the said DNA may be in sense or antisense orientation.

The cDNA of the invention may conveniently be used as a probe to isolate its genomic equivalent which may be used in a recombinant DNA for the amplification of lignin biosynthesis, the said DNA being in sense orientation.

The invention further provides a DNA comprising a transcriptional initiation region operative in plants operatively linked to a DNA sequence encoding RNA complementary to a substantial number of bases showing substantial homology to an mRNA encoding the protein produced by the gene in pMCCR6A so as to initiate production of mRNA therefrom.

Also, the invention provides a plant cell, and a plant derived therefrom having stably incorporated in its genome by transformation a DNA aforesaid in sense or antisense orientation, and the fruit and seeds of said plants.

The invention also provides a method for the regulation of lignin biosynthesis in a plant comprising stably incorporating into the genome of a plant by transformation a recombinant DNA encoding cinnamyl coenzyme A reductase from *Zea mays* in sense or antisense orientation under control of a transcriptional initiation region operative in plants.

The present invention is principally concerned with the suppression of lignin formation and, that being so, the inserted gene may be in sense or in antisense orientation, but there are instances where over-production of lignin may have an advantageous effect, for example to improve plant stalk strength and resistance to diseases, and the present invention provides means for achieving amplification of the lignin biosynthetic ability of plants.

Thus the invention relates generally to the regulation of the plant's lignin biosynthetic pathway, in which CCR plays a dominant role, in order that the production of CCR, and hence the production and composition of lignin is altered by insertion of the CCR gene, or a portion thereof (usually of 50 or more bases), in antisense orientation so that the amount of CCR for catalysing lignin synthesis is reduced.

The constructs of the invention may be inserted into plants to regulate the production of the CCR enzyme. Depending on the nature of the construct, the production of the protein may be increased, or reduced, either throughout or at particular stages in the life of the plant. It is also possible to target the expression of the gene to a specific cell types of the plant, such as the epidermis, the xylem, the roots etc.

The plants to which the present invention can be applied include commercially important food and forage plants, such as alfalfa, maize, oil seed rape, forage grasses and sunflower, and but also tree crops such as eucalyptus, pine species and poplar.

DNA constructs according to the invention preferably comprise a sequence of at least 50 bases which is homologous to the CCR of the insert in pMCCR6A. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

The preferred source of antisense RNA for use in the present invention is DNA derived from the clone pMCCR6A. The required DNA encoding antisense RNA can be obtained in several ways: by cutting an appropriate sequence of DNA from pMCCR6A (or any other source of the CCR gene); by synthesising a DNA fragment using synthetic oligonucleotides which are annealed and then ligated together in such a way as to give suitable restriction sites at each end; by using synthetic oligonucleotides in a polymerase chain reaction (PCR) to generate the required fragment with suitable restriction sites at each end. The DNA is then cloned into a vector containing upstream promoter and downstream terminator sequences, the cloning being carried out so that the DNA sequence is inverted with respect to its orientation to the promoter in the strand from which it was cut. In the new vector, the strand that was formerly the template strand becomes the coding strand, and vice versa. The new vector will thus encode RNA in a base sequence which is complementary to the sequence of pMCCR6A mRNA. Thus the two RNA strands are complementary not only in their base sequence but also in their orientations (5' to 3').

The clone pMCCR6A has been deposited at the National Collections of Industrial and Marine Bacteria, PO Box 31, of 23 St Machar Drive, Aberdeen AB2 IRY, Scotland, as a plasmid in *E. coli*, strain XL1 -Blue, under the reference NCIMB 40731 on May 23, 1995.

A source of DNA for the base sequence for transcription is the promoter of the CCR gene itself or other genes involved in lignification such as the promoter of the phenyl alanine ammonia lyase gene or its modified version which permits expression in xylem tissue, or the s-Adenosyl methionine synthase gene or the promoter of the extensin gene. Such a gene may differ from the cDNA of pMCCR6A in that introns may be present. The introns are not transcribed into mRNA (or, if so transcribed, are subsequently cut out). When using such a gene as the source of the base sequence for transcription it is possible to use either intron or exon regions. This plasmid was deposited under the provisions of the Budapest Treaty on the Deposit of Microorganisms for Patent Purposes.

A further way of obtaining a suitable DNA base sequence for transcription is to synthesise it *ab initio* from the appropriate bases, for example using Sequence-ID-1. Recombinant DNA and vectors according to the present invention may be made as follows. A suitable vector containing the desired base sequence for transcription (for example pMCCR6A) is treated with restriction enzymes to out cut the sequence. The DNA strand so obtained is cloned (in reverse orientation) into a second vector containing the desired promoter sequence (for example cauliflower mosaic virus 35S RNA promoter or the bean PAL promoter, Bevan et al, EMBO J.8, 1899–1906 1989) and the desired terminator sequence (for example the 3' of the *Agrobacterium tumefaciens* nopaline synthase gene. In this invention we may use both constitutive promoters (such as cauliflower mosaic virus 35S RNA) and inducible or developmentally regulated promoters (such as the PAL gene promoter) as circumstances require. Use of a constitutive promoter will tend to affect functions in all parts of the plant: while by using a tissue specific promoter, functions may be controlled more selectively. The use of a tissue-specific promoter, has the advantage that the antisense or sense RNA is only produced in the tissue in which its action is required.

Vectors according to the invention may be used to transform plants as desired, to make plants according to the invention. Dicotyledonous plants, such as alfalfa, oil seed rape etc, may be transformed by *Agrobacterium* Ti plasmid technology, for example as described by Bevan (1984) Nucleic Acid Research, 12, 8711–8721. Such transformed plants may be replicated sexually, or by cell or tissue culture.

Poplar and aspen transformation using *Agrobacterium tumefaciens* can be performed as described by De Block [Plant Physiol. (1990) 93:1110–1116]. Stem internode pieces are used as a tissue source for incubation with an *Agrobacterium tumefaciens* strain (C58CRifR(pMP90.) harbouring chimeric marker genes (bar/neo) on its non-oncogenic T-DNA. For the aspen clone (*Populus alba*×*P. tremula*; clone 357, Afocel) and the poplar clone (*Populus trichocarpa*×*P. deltoides*; clone 064, Afocel), transgenic shoots were obtained 3 months and 6 months after incubation, respectively.

The degree of production of RNA in the plant cells can be controlled by suitable choice of promoter sequences, or by selecting the number of copies, or the site of integration, of the DNA sequences according to the invention that are introduced into the plant genome. In this way it may be possible to modify lignification to a greater or lesser extent.

The constructs of our invention may be used to transform cells of both monocotyledonous and dicotyledonous plants in various ways known to the art. In many cases such plant cells (particularly when they are cells of dicotyledonous plants) may be cultured to regenerate whole plants which subsequently reproduce to give successive generations of genetically modified plants. Examples of genetically modified plants according to the present invention include, alfalfa, oil seed rape, sunflower, sorghum, maize, festuca, and trees such as eucalyptus, poplar, and pine.

It could be envisaged that a vector the same or similar to pIGPD6 (FIG. 1) be used for transforming monocotyledonous plants using various ways known to the art. Such a method could involve the use of silicon carbide whiskers as described in The Plant Journal (1994) 6(6), 941–948. A possible promoter sequence could be a constitutive promoter such as the polyubiquitin promoter or the ubiquitin extension protein promoter or a modification of these promoters. Other possible promoters could be an inducible or developmentally regulated promoters such as the PAL gene promoter or the endogenous CAD gene promoter. The ADH1 intron could be inserted next to the promoter to enhance expression. Use of a constitutive promoter will tend to affect finctions in all parts of the plant: while by using a tissue specific promoter, functions may be controlled more selectively. The use of a tissue-specific promoter, has the advantage that the sense RNA is only produced in the tissue in which its action is required.

The invention will now be described further with reference to the accompanying drawings, in which.

Figure 1:
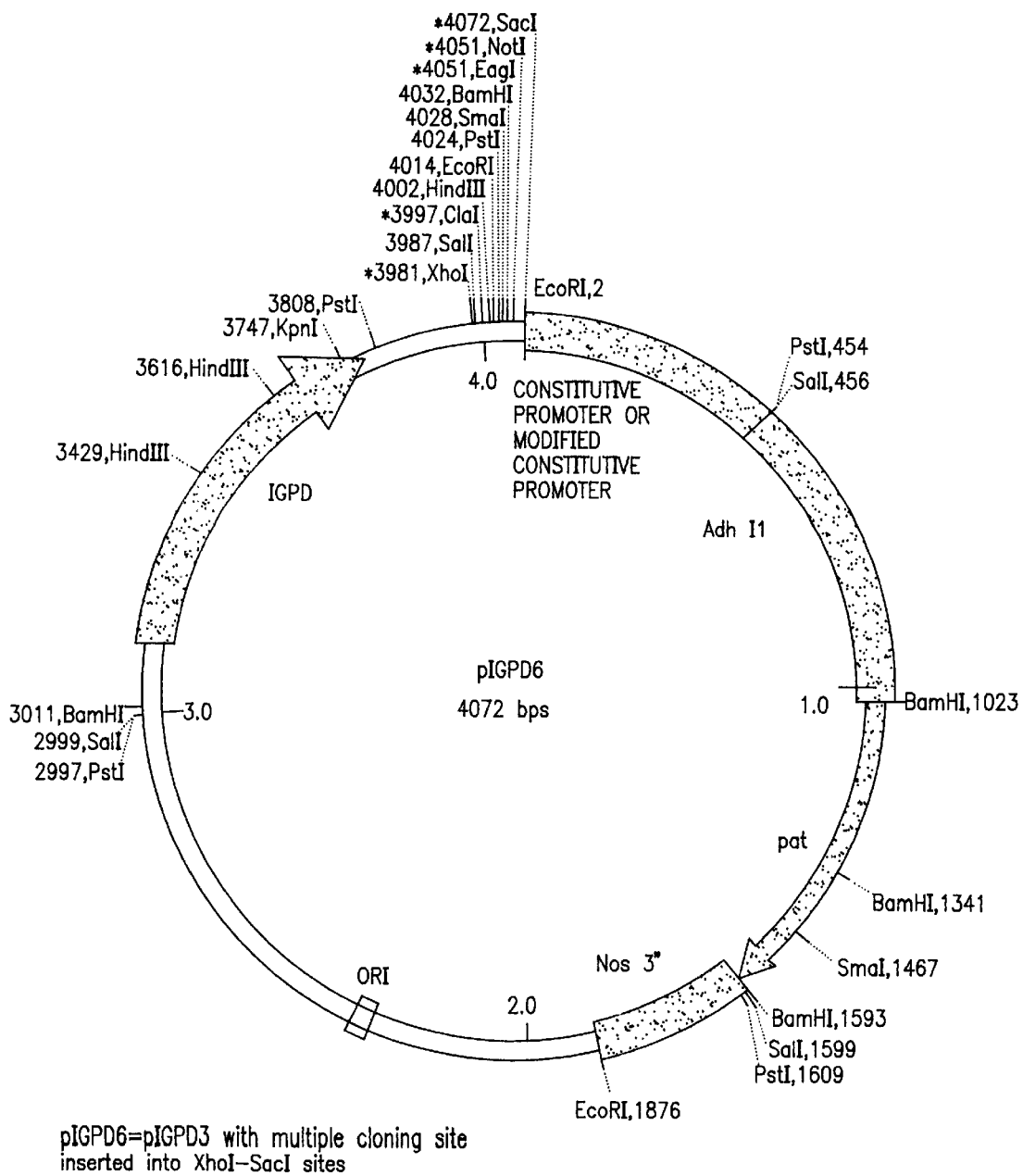
FIG. 1 is a map of the plasmid pIGPD6.

Isolation of maize(*Zea mays*) Cinnamyl CoA Reductase (CCR) cDNA

1. Screening a Maize cDNA Library With a Heterogous Probe

The library used was a commercially available one obtained from Stratagene (Catalog #937005). In it, cDNA from B73 inbred maize leaf and sheath was cloned unidirectionally (ECoRI/Xhol) in the Uni- ZAPTMXR vector.

The library (850,000 pfu) was plated using XL-1 blue cells on 150 mm plates. The library was screened with a radiolabelled heterologous CCR CDNA probe from Eucalyptus. Hybridisation was carried out in Blotto (5xSSPE, 0.25% Marvel and 0.1% SDS) for 16 hrs at 55° C. Filters were washed in 6xSSC, 0.1% SDS at 55° C. No positives were obtained from this screen.

2. Screening a Maize cDNA Library With Degenerate Oligonucleotides

The library was then screened with degenerate oligonucleotides designed from sequence homology between the Eucalyptus CCR and a sequence from Arabidopsis (see Table 1). End labelled oligonucleotides CCR11, CCR12 and CCR14 were used to screen the library plated above. Hybridisation was carried out in Blotto for 16 hrs at 42° C. The filters were washed in 6×SSC, 0.1% SDS at 42° C. No positives were obtained in this screen.

TABLE 1

Degenerate oligonucleotides based on sequences from Eucalyptus and Arabidopsis

Oligonucleotides shown in a 5'–3' direction (I = Inosine)

SEQUENCE-ID-2 (CCR11)

```
ACI  AAA  AAT  TGG  TAT  TGT  TAT  GGI  AA
     G    C         C    C    C
```

SEQUENCE-ID-3 (CCR12)

```
TA  IGT  TTT  IGC  IGA  ICC  IGT  IAA  ATA  CTT
    C         CT                  G    G    T
```

SEQUENCE-ID-4 (CCR13)

```
GCI  TCI  TGG  ATI  GTI  AAA  CTI  CTI  CTI  GA
     AG                  G    T    T    T
```

SEQUENCE-ID-5 (CCR14)

```
AC  IGG  ATT  IAA  IAC  IAC  IAI  ATC  IAC  ICC
    G    G                        G
```

3. Generation of a Maize Specific Probe

The approach of using heterologous probes in maize was clearly unsuccessfull and our next approach was to generate a maize specific probe. The four degenerate oligonucleotides CCR11, CCR12, CCR13 and CCR14 were used in different combinations to amplify CCR sequences from maize cDNA. Of the different combinations only one (CCR11 and CCR12) gave a product. The size of the product was 184bp (determined by sequencing) and was the expected size with these primers. The product was cloned into Invitrogen's PCR II vector and was sequenced to investigate its identity. Comparison of the sequence with Eucalyptus and Poplar CCR suggested the product was maize CCR.

The 200 bp product was used to screen the Stratagene maize cDNA library. The library (500,000 pfu) was replated and probed with the radiolabelled maize 200 bp PCR product. Hybridisation was carried out in Blotto for 16 hrs at 65° C. The filters were washed in 0.1×SSC, 0.1×SDS at 65° C. Three positives were obtained MCCR6A, MCCR8A and MCCR9B. The Bluescript plasmid was recovered by in vivo excision. Sequencing of the clones at the 3' end suggested they were identical except MCCR9B had a missing ATAGC prior to the poly A tail. Further sequencing of MCCR6A confirmed its identity as a maize CCR. The pMCCR6A is 713 bp (excluding the poly A+) and 608 bp is coding sequence. The clone is not full length and contains the 3' region suggesting that the 5' region may have been lost by an unprotected EcoR1 site within the middle of the clone during the construction of the cDNA library. The clone has been fully sequenced and the sequence is enclosed. The sequence of the PCR product is also enclosed. In this PCR product the bases 1–27 and 157–184 are the synthetic primers used in the PCR reaction. Bases 28–183 are identical to pMCCR6A except for one base change (T changed to a C) at position 129. This base change has no effect on the amino acid sequence (eg the serine remains unchanged). Alignment of pMCCR6A to other CCR sequences shows the sequence to be 54–58% homologous at the amino acid level and 5 63–64% homologous at the DNA level.

A database search using the pMCCR6A sequence showed that proteins with greatest homology were dihydroflavonol reductases giving a highest homology of 29% at the amino acid level.

Figure 2:
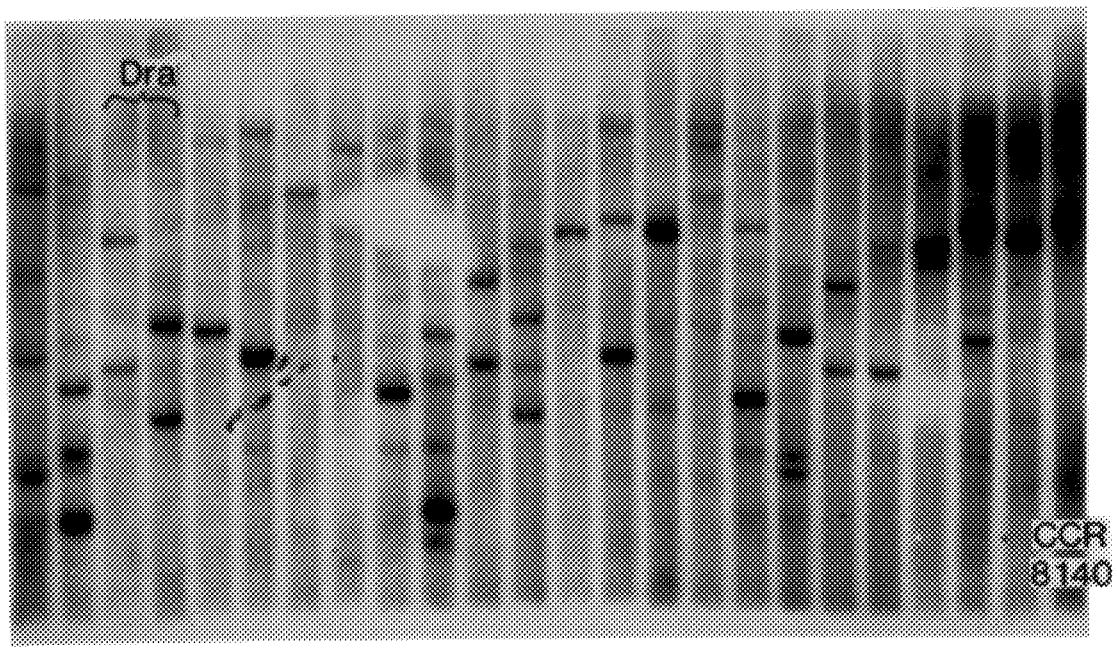
FIG. 2 shows a Southern analysis of genomic DNA prepared from a recombinant maize inbred line.

Southern analysis of genomic DNA prepared from a recombinant maize inbred line suggests that the maize CCR is present at two major locus in the maize genome. Subsequent mapping of these two genes shows that the first locus maps to Chromosome 5 and the second maps to Chromosome 4. (See FIG. 2)

SEQUENCE-ID-1

```
  1 GGC ACG AGA AGA GCA CCG AGA ACT GTT ACT GCT ACG CAA AGA CGG
    CCG TGC TCT TCT CGT GGC TCT TGA CCA TGA CGA TGC GTT TCT GCC

46 TGC CGG AGC AGG GCG CGT GGG AGG CGG CGC GGG CGC GGG GGC TGG
    ACC GCC TCG TCC CGC GCA CCC TCC GCC GCG CCC GCG CCC CCG ACC

91 ACC TGG CGG TGG TCA TCC CGG TGG TGG TGC TCG GCG AGC TGC TGC
    TGG ACC GCC ACC AGT AGG GCC ACC ACC ACG AGC CGC TCG ACG ACG

136 AGC CCA GTA TGA ACA CCA GCA CCC TGC ACA TCC TCA AGT ACC TCA
    TCG GGT CAT ACT TGT GGT CGT GGG ACG TGT AGG AGT TCA TGG AGT

181 CGG GAC AGA CAA AGG AGT ACG TCA ACG AGT CGC ACG CCT ACG TCG
    GCC CTG TCT GTT TCC TCA TGC AGT TGC TCA GCG TGC GGA TGC AGC

226 ACG TCA GGG ACG CCG CCG AGG CGC ACG TCA GGG TCG TGG AGG CGC
    TGC AGT CCC TGC GGC GGC TCC GCG TGC AGT CCC ACG ACC TCC GCG

271 CCG GAG CCG GCG GCC GCC GGT ACG TCT GCG CCG AGC GCA CCC TGC
    GGC CTC GGC CGC CGG CGG CCA TGC AGA CGC GGC TCG CGT GGG ACG

316 ACC GCG GCG AGC TCT GCC GCA TCC TCG CCG GAC TCT TCC CGG AGT
    TGG CGC CGC TCG AGA CGG CGT AGG AGC GGC CTG AGA AGG GCC TCA

361 ACC CTA TTC CGA CAA GGT GCA AGG ATC AGG TGA ACC CAC TGA AGA
    TGG GAT AAG GCT GTT CCA CGT TCC TAG TCC ACT TGG GTG ACT TCT

406 AGG GCT ACA AGT TTA CGA ACC AAC CTC TGA AGG ACC TTG GCG TCA
    TCC CGA TGT TCA AAT GCT TGG TTG GAG ACT TCC TGG AAC CGC AGT
```

-continued
SEQUENCE-ID-1

```
451 AGT TCA CGC CAG TTC ATG GGT ACC TGT ACG AAG CAG TGA AGT CCC
    TCA AGT GCG GTC AAG TAC CCA TGG ACA TGC TTC GTC ACT TCA GGG

496 TTC AAG ACA AGG GGT TCC TCC CGA AGA CAT CTG GCG CCA AGG TGC
    AAG TTC TGT TCC CCA AGG AGG GCT TCT GTA GAC CGC GGT TCC ACG

541 CTG AAC GAC GCA GCT GCC TGC CTC AAA CGA CAT CAC AGC CAC CAC
    GAC TTG CTG CGT CGA CGG ACG GAG TTT GCT GTA GTG TCG GTG GTG

586 CCG AAA TCG TTT CGA AAC TTT GAG GTG GAT CTG CAC ACG TGC TCA
    GGC TTT AGC AAA GCT TTG AAA CTC CAC CTA GAC GTG TGC ACG AGT

631 AAC TGG CCA TGT GTT TTT TTG TCA GAC AAG CCG TTC ATT TGA TTG
    TTG ACC GGT ACA CAA AAA AAC AGT CTG TTC GGC AAG TAA ACT AAC

676 GTT ATT AAA AGA TTT TGG GCA GTC TGT TCT TAC ATA GC
    CAA TAA TTT TCT AAA ACC CGT CAG ACA AGA ATG TAT CG
```

SEQUENCE-ID-2

```
ACI AAA AAT TGG TAT TGT TAT GGI AA
 G       C        C   C   C
```

SEQUENCE-ID-3

```
TA IGT TTT IGC IGA ICC IGT IAA ATA CTT
    C        CT           G   G   T
```

SEQUENCE-ID-4

```
GCI TCI TGG ATI GTI AAA CTI CTI CTI GA
         AG               G T   T   T
```

SEQUENCE-ID-5

```
AC IGG ATT IAA IAC IAC IAI ATC IAC ICC
        G   G              G
```

---

I claim:

1. A cDNA clone encoding cinnamyl coenzyme A reductase from *Zea mays* consisting of the nucleotide sequence of SEQ ID NO: 1 and variants thereof such as are permitted by the degeneracy of the genetic code, said cDNA clone comprising a coding strand and a complementary strand of DNA.

2. A recombinant DNA comprising a transcription comprising a transcription initiation sequence operative in plants operatively linked to the cDNA clone claimed in claim 1.

3. A recombinant DNA comprising a fragment of at least 50 bases of the complementary strand of the cDNA clone claimed in claim 1.

4. An isolated genomic DNA consisting of the gene encoding cinnamyl coenzyme A reductase from *Zea mays*, wherein said gene comprises the nucleotide sequence of SEQ ID NO: 1.

5. A transformed plant cell having stably incorporated in its genome the cDNA clone as claimed in claim 1 or the DNA as claimed in any one of claims 2 through 4.

6. The DNA insert of plasmid pMCCR6A, said plasmid having been deposited in an *E. coli* host under the Accession Number NCIMB 40731.

7. A plant which has been regenerated from a plant cell claimed in claim 5.

8. Fruit and seed of the plant claimed in claim 7.

9. A genetically modifed cereal or forage plant, the genome of which is modified by the insertion of a DNA as claimed in any of claims 1 through 4.

10. The genetically modified cereal or forage plant of claim 9 which is *Zea mays*.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 713 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:1:

```
GGCACGAGAA   GAGCACCGAG   AACTGGTACT   GCTACGCAAA   GACGGTGGCG   GAGCAGGGCG     60
CGTGGGAGGC   GGCGCGGGCG   CGGGGGCTGG   ACCTGGCGGT   GGTCATCCCG   GTGGTGGTGC    120
TCGGCGAGCT   GCTGCAGCCC   AGTATGAACA   CCAGCACCCT   GCACATCCTC   AAGTACCTCA    180
CGGGACAGAC   AAAGGAGTAC   GTCAACGAGT   CGCACGCCTA   CGTCGACGTC   AGGGACGCCG    240
CCGAGGCGCA   CGTCAGGGTG   CTGGAGGCGC   CCGGAGCCGG   CGGCCGCCGG   TACGTCTGCG    300
CCGAGCGCAC   CCTGCACCGC   GGCGAGCTCT   GCCGCATCCT   CGCCGGACTC   TTCCCGGAGT    360
ACCCTATTCC   GACAAGGTGC   AAGGATCAGG   TGAACCCACT   GAAGAAGGGC   TACAAGTTTA    420
CGAACCAACC   TCTGAAGGAC   CTTGGCGTCA   AGTTCACGCC   AGTTCATGGG   TACCTGTACG    480
AAGCAGTGAA   GTCCCTTCAA   GACAAGGGGT   TCCTCCCGAA   GACATCTGGC   GCCAAGGTGC    540
CTGAACGACG   CAGCTGCCTG   CCTCAAACGA   CATCACAGCC   ACCACCCGAA   ATCGTTTCGA    600
```

-continued

| AACTTTGAGG | TGGATCTGCA | CACGTGCTCA | AACTGGCCAT | GTGTTTTTTT | GTCAGACAAG | 660 |
| CCGTTCATTT | GATTGGTTAT | TAAAAGATTT | TGGGCAGTCT | GTTCTTACAT | AGC | 713 |

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:2:

ACNAARAAYT GGTAYTGYTA YGGNAA         26

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:3:

TAGYTTTSYG ACCGKNAAWT ACTT         24

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:4:

GCNTMNTGGA TNGTNAARYT NYTNYTNGA         29

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:5:

ACNGGRTTNA RNACNACNAN RTCNACNCC         29